(12) United States Patent
Ueda et al.

(10) Patent No.: US 8,449,517 B2
(45) Date of Patent: May 28, 2013

(54) ABSORBENT ARTICLE

(75) Inventors: Junko Ueda, Kagawa (JP); Koichiro Mitsui, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 387 days.

(21) Appl. No.: 12/933,620

(22) PCT Filed: Jan. 16, 2009

(86) PCT No.: PCT/JP2009/050582
§ 371 (c)(1),
(2), (4) Date: Nov. 11, 2010

(87) PCT Pub. No.: WO2009/116307
PCT Pub. Date: Sep. 24, 2009

(65) Prior Publication Data
US 2011/0054432 A1    Mar. 3, 2011

(30) Foreign Application Priority Data
Mar. 21, 2008 (JP) .................................. 2008-074215

(51) Int. Cl.
*A61F 13/49*    (2006.01)
(52) U.S. Cl.
USPC ............... 604/385.3; 604/385.01; 604/385.24
(58) Field of Classification Search
USPC ............. 604/385.01, 385.21–385.3, 392–397
See application file for complete search history.

(56) References Cited

U.S. PATENT DOCUMENTS

| | | |
|---|---|---|
| 2001/0053898 A1 | 12/2001 | Olson et al. |
| 2002/0026171 A1 | 2/2002 | Sayama et al. |
| 2003/0135187 A1* | 7/2003 | Klemp et al. ............ 604/385.01 |

FOREIGN PATENT DOCUMENTS

| | | |
|---|---|---|
| JP | 11104172 A | 4/1999 |
| JP | 2002065731 A | 3/2002 |
| JP | 2003501211 A | 1/2003 |
| JP | 2007215804 A | 8/2007 |
| WO | 0076442 A1 | 12/2000 |

OTHER PUBLICATIONS

International Search Report for PCT/JP2009/05082 mailed Apr. 14, 2009.

* cited by examiner

*Primary Examiner* — Lynne Anderson
*Assistant Examiner* — Kathryn E Ditmer
(74) *Attorney, Agent, or Firm* — Lowe Hauptman Ham & Berner, LLP (57) ABSTRACT

An absorbent article includes a rear waist region provided with a waist region elastic member attached thereto under tension. The waist region elastic member is formed with a plurality of slits each extending in a longitudinal direction and extending through the elastic member in a thickness direction thereof. The waist region elastic member is stretched in a transverse direction as the diaper is put on the wearer's body and thereupon the slits are opened up to form respective through-holes. A first graphics display region formed in combination with the slits includes note stems and note tails. Each of these note stems is contiguous to the associated through-holes. In the area nearer a crotch region than the first graphics display region, a second graphics display region is formed. The first and second graphics display regions cooperate to each other.

4 Claims, 6 Drawing Sheets

ABSORBENT ARTICLE

RELATED APPLICATIONS

The present application is a national phase of PCT/JP2009/050582, filed on Jan. 16, 2009 and is based on, and claims priority from, Japanese Application Number 2008-074215, filed Mar. 21, 2008.

TECHNICAL FIELD

The present invention relates to absorbent articles and more particularly to absorbent articles such as disposable diapers, toilet-training pants or incontinent briefs.

RELATED ART

Disposable diapers in which a waist region elastic member is formed with slits are known, for example, from JP 2002-65731 A (PATENT DOCUMENT 1). According to the disclosure of this PATENT DOCUMENT 1, the diaper comprises a liquid-absorbent chassis having a front waist region, a rear waist region, a skin-facing inner side and a garment-facing outer side; and waist region elastic sheets attached to the chassis in front and rear waist regions to extend in a transverse direction, respectively. The waist region elastic sheets are formed with a plurality of slits extending in a longitudinal direction. These slits extend through the waist region elastic sheets and the chassis from the skin-facing inner side to the garment-facing outer side in a thickness direction thereof. By forming the slits in this manner, it is possible to prevent inside of the diaper from becoming stuffy.

Disposable diapers provided on its garment-facing outer side with character graphics are known, for example, from JP 2003-501211 T (PATENT DOCUMENT 2). According to the disclosure of this PATENT DOCUMENT 2, the diaper is provided with usual graphics adapted to be visible already before use of the diaper and latent graphics adapted to become visible upon excretion such as urination so that these usual graphics and latent graphics may be meaningfully related to each other. Such meaningful relationship can induce parent-child verbal interaction.
PATENT DOCUMENT 1: JP 2002-65731 A
PATENT DOCUMENT 2: JP 2003-501211 T

DISCLOSURE OF THE INVENTION

Problem to be Solved by the Invention

During exchange of the diaper, the wearer, particularly a baby may often get bored and vigorously move his or her body. To keep the baby from getting bored in such occasions, it will be effective to bring the variable graphics into view and to speak to the baby.

However, in the case of the diaper disclosed by PATENT DOCUMENT 1, the waist region elastic sheet is stretched as the fresh diaper is put on the baby's body and thereupon the slits are pulled toward both sides to form the through-holes. Change of the graphics occurring in the course of exchanging the soiled diaper with the fresh one is nothing but such formation of the through-holes in the waist region elastic sheet. Regrettably, it will be difficult for these through-holes to attract the baby's attention and to induce parent-baby dialogue.

In the case of the diaper disclosed by PATENT DOCUMENT 2, the latent graphics is visualized because of excretion such as urination but not in the course of exchanging the soiled diaper with the fresh one.

In view of the problem as has been described above, it is a principal object of the present invention to provide an absorbent article improved so that the wearer can visually recognize graphics adapted to change in the course of exchanging the soiled diaper with the fresh one.

Measure to Solve the Problem

The object set forth above is achieved, according to the present invention, by an improvement in the absorbent article comprising a chassis having a longitudinal direction, a transverse direction, a skin-facing side, a garment-facing side, a front waist region, a rear waist region and a crotch region extending between the front and rear waist regions, these three regions arranged continuously in the longitudinal direction; and a waist region elastic member attached under tension along an end of at least one of the front and rear waist regions.

The improvement according to the present invention is characterized in that the waist region elastic member includes slits extending in the longitudinal direction therethrough in its thickness direction and the slits are adapted to be stretched in the transverse direction under the effect of the waist region elastic member to form through-holes; and the waist region elastic member further includes a first graphics display region defined on the garment-facing side in combination with respective peripheries of said slits so that the first graphics display region may cooperate with the through-holes to form a graphic art.

According to one preferred embodiment of the present invention, the absorbent article further including a second graphics display region defined on the garment-facing side of the front and/or rear waist region and formed with the slits and a graphic art meaningfully related with the graphic art in the first graphics display region is displayed in the second graphics display region.

According to another preferred embodiment of the present invention, the chassis includes an inner sheet defining a side facing the article wearer's body and an outer sheet defining a side facing the article wearer's clothes and said waist region elastic member is sandwiched between the inner and outer sheets and the through-holes extend through the inner and outer sheets also in the thickness direction thereof.

According to still another preferred embodiment of the present invention, the first and second graphics display regions are formed on the front waist region.

Effect of the Invention

The waist region elastic member is formed with the slits each extending in the longitudinal direction through this member in its thickness direction and these slits are stretched in the transverse direction under the effect of the waist region elastic member to form the through-holes. The first graphics display region defined in combination with the slits is formed on the garment-facing side so that this first graphics display region may cooperate with the through-holes to display a graphic art. With such arrangement, the waist region elastic member is stretched to form the through-holes as the absorbent article is put on the article wearer's body and thereupon the graphics on the first graphics display region changes in cooperation with these through-holes. Thus it is possible to have the article wearer, particularly a baby be aware of a change appearing on the graphic art during use of the article and to promote parent-baby dialogue without making the baby bored. Such possibility contributes also to intellectual training of the baby.

The article is further provided with a second graphics display region defined on the garment-facing side of the front and/or rear waist region and formed with the slits and graphics adapted to be meaningfully related with the graphics in the first graphics display region is or are displayed in the second graphics display region or the second graphics display regions. With such arrangement, the apprehension that the article wearer might get bored in the course of exchanging the stained article with the fresh one can be further reliably restricted and, particularly in the case where the article wearer is a baby, such arrangement is expected to contribution to the intellectual training of the baby.

The waist region elastic member is sandwiched between the inner and outer sheets cooperating with each other to form the chassis and the through-holes extend through the inner and outer sheets also in the thickness direction thereof. Such arrangement facilitates the through-holes to be visually recognized and, in addition, clears up the graphics displayed in the first graphics display region.

The first and second graphics display regions are formed on the front waist region so that the article wearer can easily recognize the graphics during use of the article.

IDENTIFICATION OF REFERENCE NUMERALS USED IN THE DRAWINGS 1 diaper
2 chassis
3 waist region elastic members
4 leg elastic members
5 front waist region
6 rear waist region
7 crotch region
8 inner sheet
9 outer sheet
10 liquid-absorbent structure
16 slits
23 first graphics display region
24 second graphics display region
27 through-holes
28 front waist region elastic member
29 rear waist region elastic member

DETAILED DESCRIPTION OF THE PREFERRED EMBODIMENTS

Details of the present invention will be more fully understood from the description of a disposable diaper as one of the typical embodiments of the absorbent article according to the present invention.

First Embodiment

Figure 1:
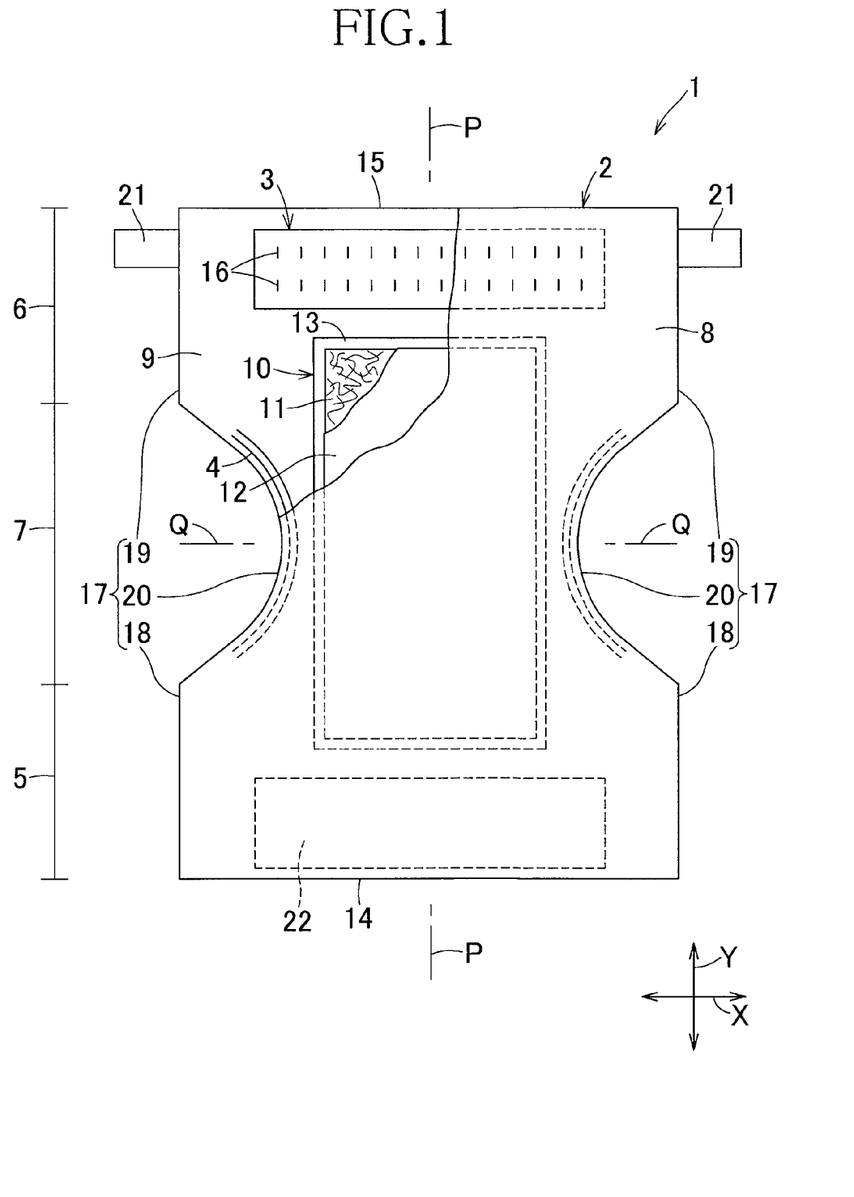
FIG. 1 is a plan view of a flatly developed diaper according to a first embodiment as viewed from the skin-facing side.

FIG. 1 is a plan view of a flatly developed diaper 1 of so-called open-type partially cutaway for convenience of illustration. As shown, the diaper 1 comprises a chassis 2, a waist region elastic member 3 and leg elastic members 4. In another respect, the chassis 2 has a front waist region 5, a rear waist region 6 and a crotch region 7 extending between these front and rear waist regions continuously arranged in a longitudinal direction Y. A direction extending orthogonally to the longitudinal direction Y is designated herein as a transverse direction X.

In still another respect, the chassis 2 includes an inner sheet 8 defining a skin-facing inner side and an outer sheet 9 defining a garment-facing outer side wherein, at least in the crotch region 7, a liquid-absorbent structure 10 is sandwiched between the inner and outer sheets 8, 9. The inner and outer sheets 8, 9 may be formed of, for example, an air-permeable nonwoven fabric.

The liquid-absorbent structure 10 comprises a liquid-absorbent core material 11 formed of, for example, a mixture of fluff pulp fibers and super-absorbent polymer particles and a dispersant sheet 12 such as a tissue paper adapted to wrap the liquid-absorbent core material 11. Between the liquid-absorbent structure 10 and the outer sheet 9, a leak-barrier sheet 13 formed of, for example, a plastic film is sandwiched to prevent body waste such as urine from leaking out of the diaper 1.

The chassis 2 includes front and rear ends 14, 15 opposed to each other in the longitudinal direction Y and extending in the transverse direction X wherein the waist region elastic member 3 is attached to the chassis 2 along the rear end 15. The waist region elastic member 3 is formed of an elastically stretchable and contractible sheet and attached to the chassis 2 under tension in the transverse direction X.

The waist region elastic member 3 is formed with a plurality of slits 16 each extending in the longitudinal direction Y. These slits 16 are arranged in two rows opposed to each other in the longitudinal direction Y and arranged substantially at regular intervals in the transverse direction X. It should be appreciated that the arrangement of these slits 16 is not limited to such two row arrangement and may be appropriately changed depending on various factors such as a size and material. The slits 16 are formed to extend through the inner and outer sheets 8, 9 from the skin-facing inner side to the garment-facing outer side in the thickness direction thereof.

The chassis 2 comprises side edges 17 opposed to each other in the transverse direction X and extending in the longitudinal direction Y. These side edges 17 comprise front waist region's side edges 18 defined in the front waist region 5, rear waist region's side edges 19 defined in the rear waist region 6 and leg side edges 20 defined in the crotch region 7. The leg side edges 20 curve convexly toward a longitudinal center line P-P bisecting a dimension of the diaper 1 in the transverse direction X so that the chassis 2 may having a concave shape curved inwardly.

The side edges 17 are respectively provided with a plurality of the leg elastic members 4 attached between the inner and outer sheets 8, 9 under tension. These leg elastic members 4 allow the respective leg side edges 20 to fit around the article wearer's legs thereby allow it to prevent body waste such as urine from leaking out beyond the leg-openings' peripheries.

On appropriate positions along the respective rear waist region's side edges 9, tape fasteners extending in the transverse direction X in the form of a hook member 21 constituting a so-called mechanical fastener is attached to the outer sheet 9. In the front waist region 5, a loop member 22 constituting the mechanical fastener adapted to be engaged with the hook member 21 is attached to the outer sheet 9.

Figure 2:
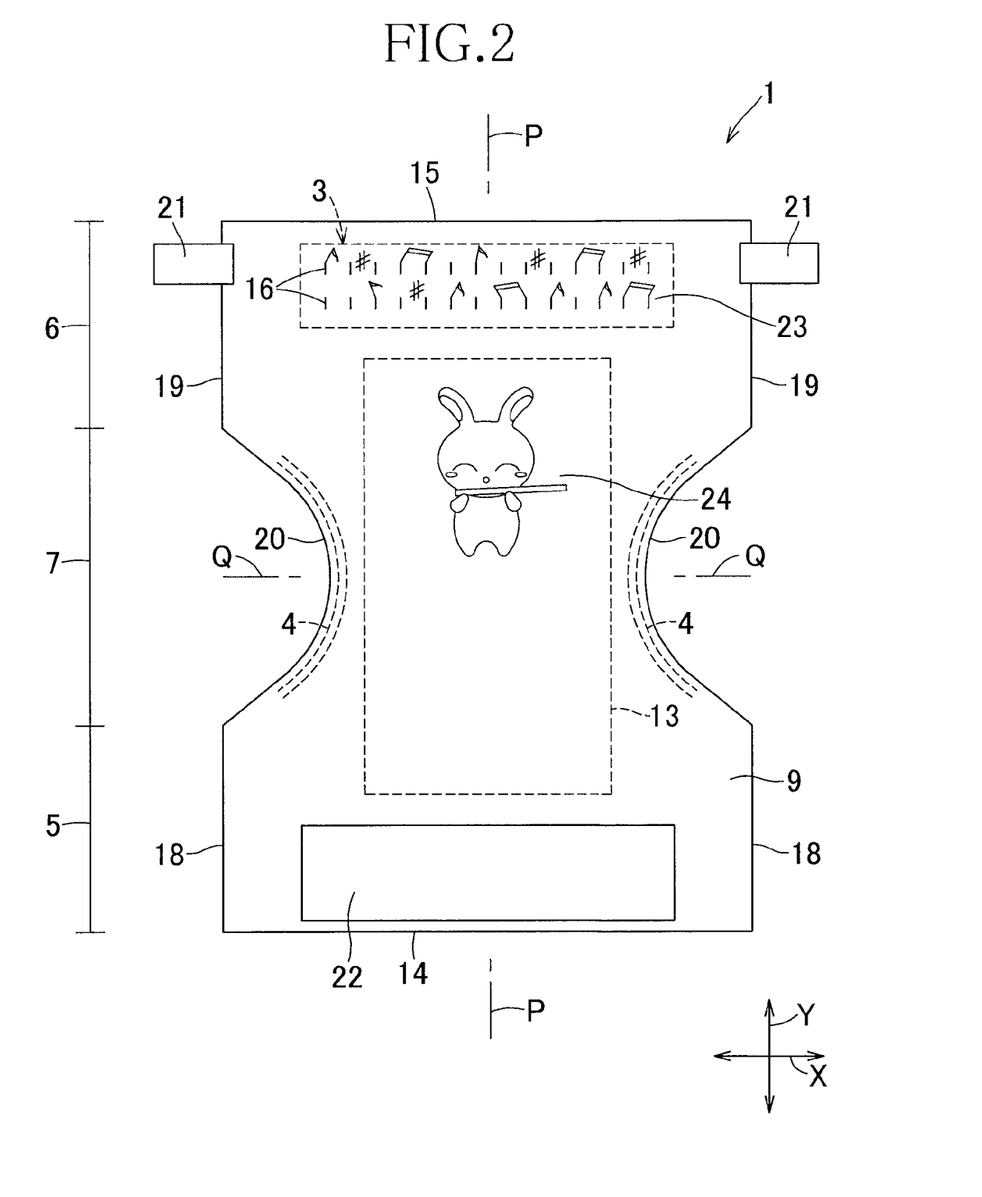
FIG. 2 is a plan view of the flatly developed diaper as viewed from the garment-facing side.

FIG. 2 is also a plan view of the flatly developed diaper 1 but as viewed from the side of the outer sheet 9. As shown, graphic elements constituting a first graphics display region 23 are distributed to be mixed with the slits 16. In the first graphics display region 23 comprises a plurality of notes each having a stem and a tail but having not a head. The respective stems are printed to be connected to the associated slits 16. These note stems and note tails may be printed on the waist region elastic member 3 to be visually recognized through the outer sheet 9 or directly on the outer sheet 9. It should be noted here that, if these note stems and note tails are printed on the waist region elastic member 3, it is desired to use the transparent or translucent outer sheet 9 to assure the graphics elements to be visually recognized.

The diaper 1 is formed on the outer sheet 9 with a second graphics display region 24 located nearer a transverse center line Q-Q bisecting a dimension of the chassis 2 in the longitudinal direction Y than the first graphics display region 23. In other words, the second graphics display region 24 extends from the rear waist region 6 toward the crotch region 7. In the second graphics display region 24, the character playing an instrument is printed. The second graphics display region 24 may be printed directly on the outer sheet 9 or, for example, on the side of the leak-barrier sheet 13 facing the outer sheet 9. It should be noted here that, if the second graphics display region is printed on the leak-barrier sheet 13, it is desired to use the transparent or translucent outer sheet 9 so that the graphics can be visually recognized through the outer sheet 9.

Figure 3:
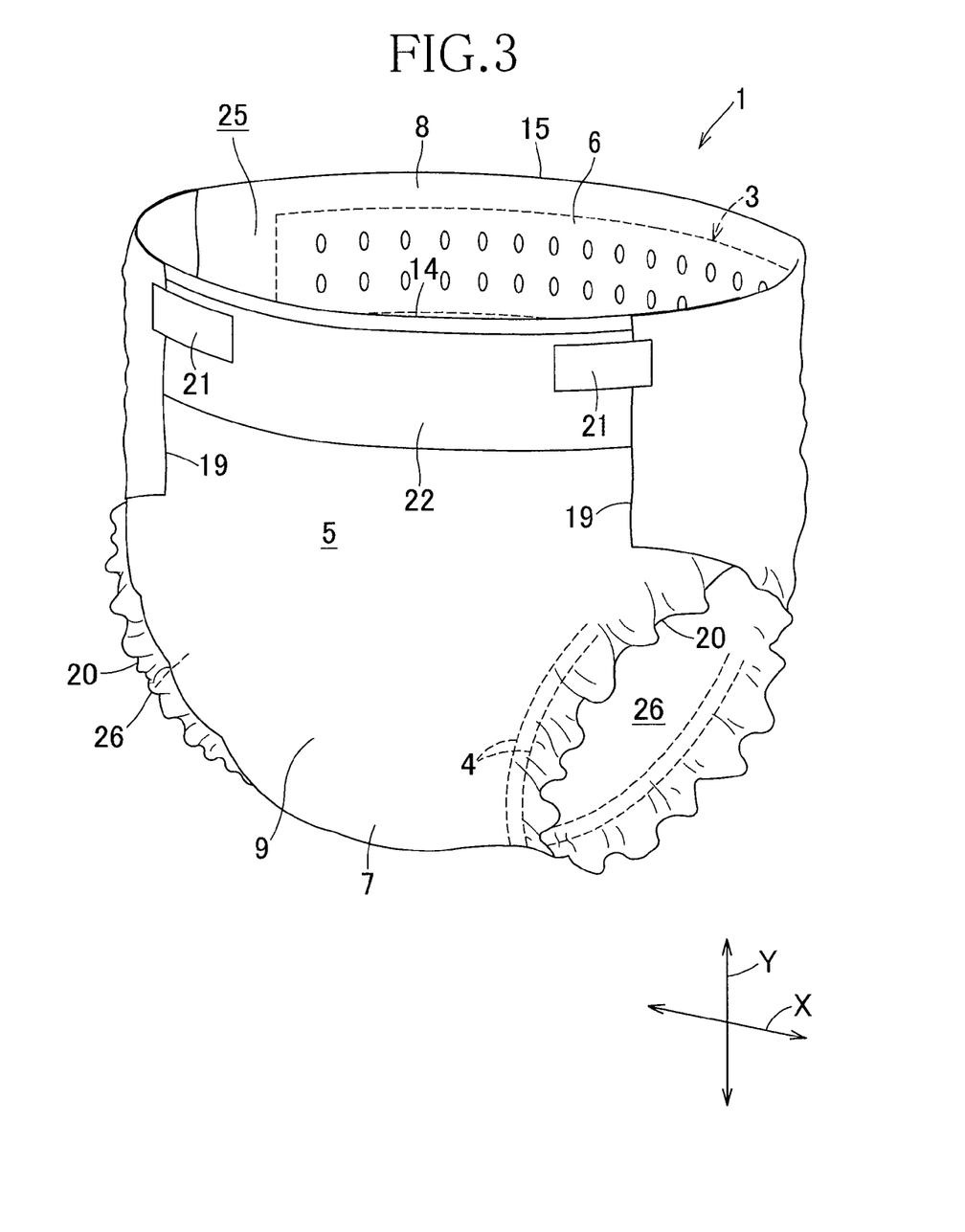
FIG. 3 is a perspective front view of the diaper put on the wearer's body.
Figure 4:
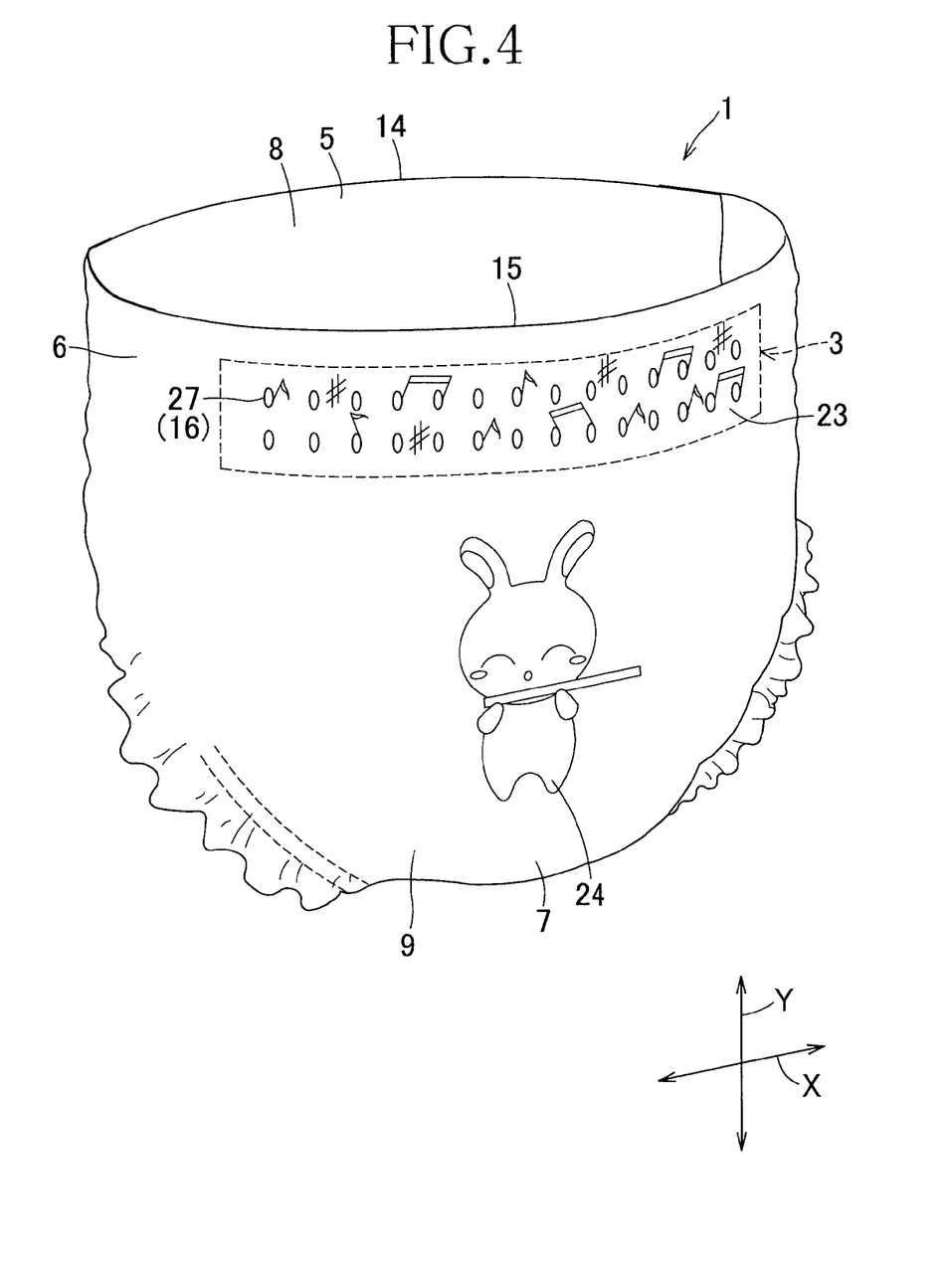
FIG. 4 is a perspective rear view of the diaper put on the wearer's body.

FIGS. 3 and 4 are perspective views illustrating the aforementioned diaper 1 being put on the wearer's body wherein FIG. 3 shows a front view of the diaper 1. To put the diaper 1 on the wearer's body, the inner sheet 8 is placed against the wearer's skin, the hook member 21 is pulled to stretch the waist region elastic member 3 and, in this state, the hook member 21 is engaged with the loop member 22. Thereby the diaper 1 is shaped in pant-type whereupon a waist-opening 25 and a pair of leg-openings 26 are formed.

FIG. 4 shows the rear view of the diaper 1. As shown, the waist region elastic member 3 is stretched as the diaper 1 is put on the wearer's body and therefore the slits 16 formed in the waist region elastic member 3 are pulled in the transverse direction X whereupon the inner and outer sheets 8, 9 are also pulled in the transverse direction X. Consequently, the slits 16 are opened up to form through-holes 27, respectively, each extending from the skin-facing side of the diaper 1 to the garment-facing side of the diaper 1. The first graphics display region 23 includes the note stems contiguous to the associated slits 16 and the note tails. The slits 16 having been opened up to form the respective through-holes 27 are now recognized as note heads and cooperate with the associated stems and tails to complete the musical notes.

The graphics which was latent when the diaper 1 was put on the wearer's body now becomes visible and the wearer can recognize that the graphics has change. Particularly in the case where the wearer is a baby, it is possible to bring the baby's attention to such change occurring in the graphics and thereby to exchange the stained diaper 1 with the fresh one smoothly without boring the baby.

The second graphics display region 24 is located near the transverse center line Q-Q than the first graphics display region 23 and, in this second graphics display region 24, a character plying an instrument is printed. Such unique combination of two graphics display regions 23, 24 is effective to make the baby think as if the musical notes appearing in the first graphics display region 23 come out from the character's instrument, in other words, the character is actually playing the instrument. Such meaningful relationship between the first graphics display region 23 and the second graphics display region 24 can effectively attract the baby's interest and prevent the wearer might get bored.

In addition, the through-holes 27 formed from the slits 16 serve to let off an amount of vapor generated inside the diaper 1 and thereby to prevent the inside of the diaper 1 from becoming stuffy.

While the waist region elastic member 3 is attached to the rear waist region 6 according to the present embodiment, it is possible to attach the waist region elastic member 3 to the front waist region 5 or to both the front and rear waist regions 5, 6. If the waist region elastic member 3 is attached to both the front and rear waist regions 5, 6, any one of these front and rear waist regions 5, 6 may be formed with the slits 16 or both of these waist region elastic members 3 may be formed with the slits 16.

While the slits 16 are formed to extend through the inner and outer sheets 8, 9 and the waist region elastic member 3 according to the present embodiment, it is possible to form these slits 16 to extend through at least the waist region elastic member 3 in the thickness direction without extending through the inner and outer sheets 8, 9 in the thickness direction.

Second Embodiment

Figure 5:
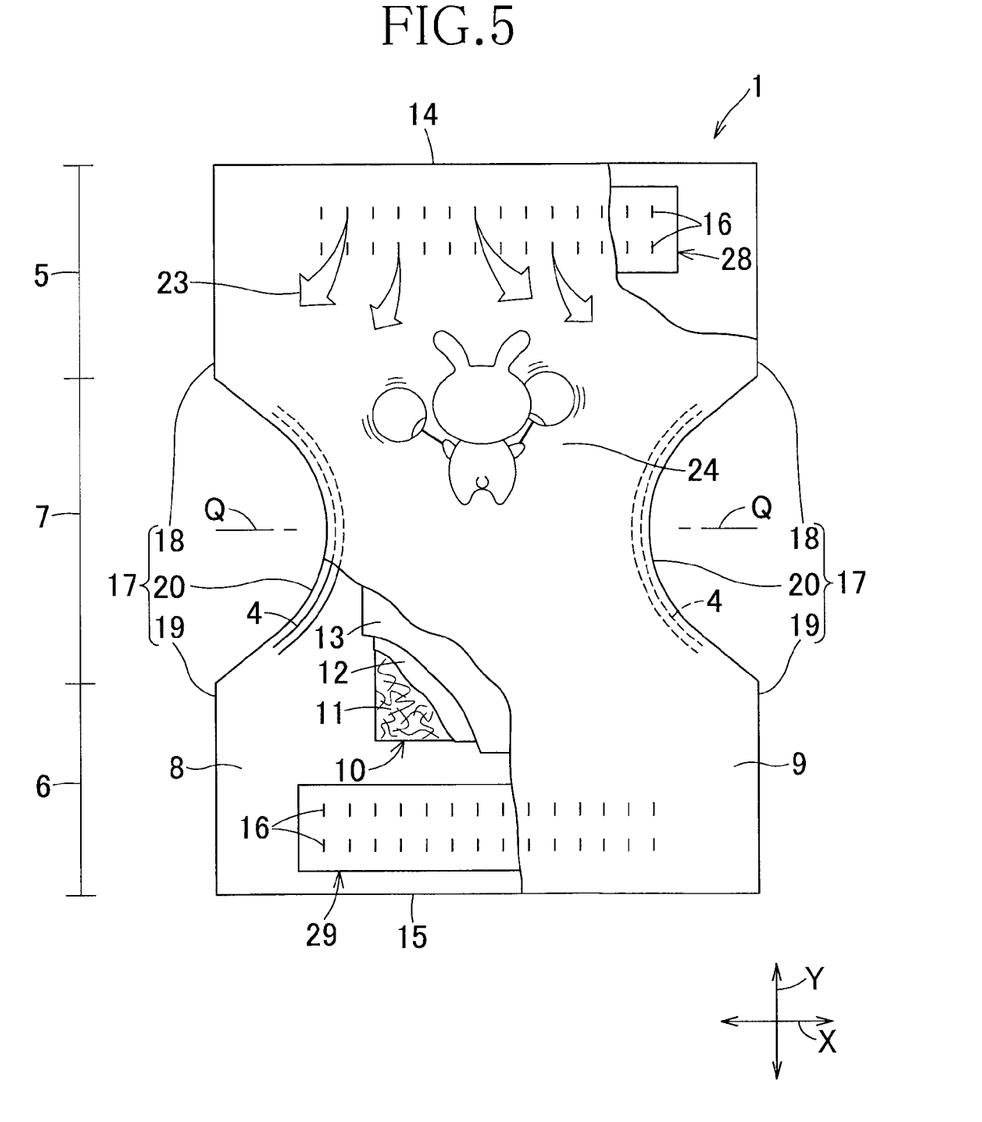
FIG. 5 is a plan view of the flatly developed diaper according to a second embodiment as viewed from the garment-facing side.
Figure 6:
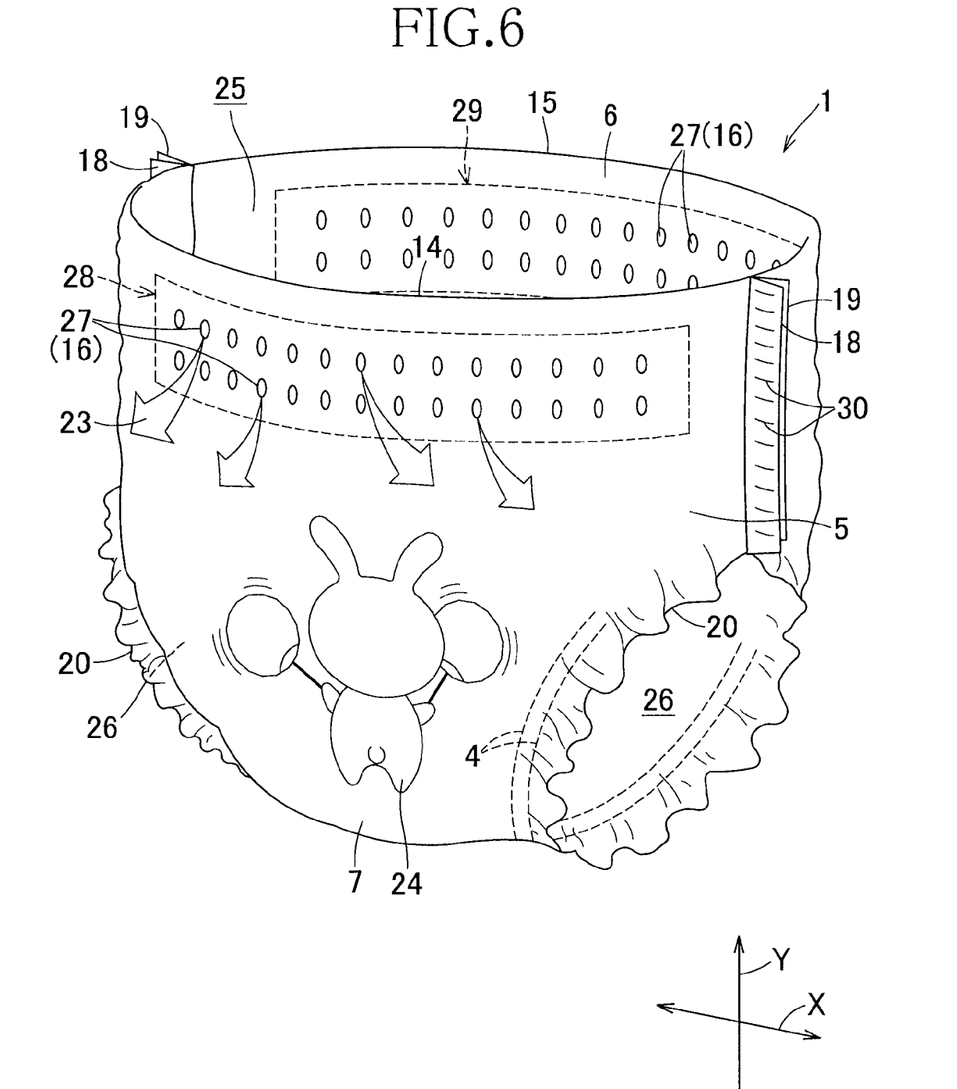
FIG. 6 is a perspective front view of the diaper put on the wearer's body.

FIGS. 5 and 6 illustrate a second embodiment of the present invention. This second embodiment is similar to the first embodiment except that both the first and second graphics display regions 23, 24 are formed on the front waist region 5 and so-called pullon-pant type is used as the diaper 1. The components or members similar to those in the first embodiment will be not described in details.

FIG. 5 is a flatly developed plan view as viewed from the side of the outer sheet 9 and with the respective elastic members or elastic members being held in stretched states. According to this second embodiment, both the front waist region 5 and the rear waist region 6 are provided along the front and rear ends 14, 15 with front and rear waist regions elastic members 28, 29. The front and rear waist regions elastic members 28, 29 are formed of elastically stretchable and contractible sheets and sandwiched between the inner and outer sheets 8, 9 and attached under tension in the transverse direction X.

The front and rear waist regions elastic members 28, 29 are formed with a plurality of slits 16 each extending in the longitudinal direction Y. These slits 16 are arranged in two rows opposed to each other in the longitudinal direction Y and arranged substantially at regular intervals in the transverse direction X. The slits 16 are formed to extend through the inner and outer sheets 8, 9 and the front and rear waist regions elastic members 28, 29 from the skin-facing inner side to the garment-facing outer side in the thickness direction thereof.

On the outer sheet 9, the first graphics display region 23 is formed in combination with the slits 16. The first graphics display region 23 includes a several arrows which pop out from some of the slits 16 toward the transverse center line Q-Q. The diaper 1 is formed on the outer sheet 9 with a second graphics display region 24 located near the transverse center line Q-Q than the first graphics display region 23. In other words, the second graphics display region 24 extends from the from waist region 5 toward the crotch region 7. In the second graphics display region 24, the character using paper fans is printed.

FIG. 6 is a perspective view of the diaper put on the wearer's body. In the case of the pants-type diaper 1 shown by FIG. 6, the front waist region's side edges 18 are bonded to the rear waist region's side edges 19 at arrays of joints 30 to shape the diaper 1 in pants-type. FIG. 6 is a perspective front view of the pant-type diaper 1. The front and rear waist regions elastic members 28, 29 are stretched as the diaper 1 is put on the wearer's body and therefore the slits 16 formed in the front and rear waist regions elastic member 28, 29 are pulled in the transverse direction X whereupon the inner and outer sheets 8, 9 to which the front and rear waist elastic members 28, 29 are bonded are also pulled in the transverse direction X. Consequently, the slits 16 are opened up to form through-holes 27, respectively, each extending through the diaper 1 from its skin-facing side to its garment-facing side. In the front waist region 5, the first graphics display region 23 is formed in combination with the slits 16 and, therefore, when the slits 16 are opened up to form the through-holes 27, the slits 16 cooperate with the graphics to create a false sense as if the arrows pop-up from the through-holes 27. As a consequence, the wearer surely recognizes the graphics changing in this manner without getting bored.

An area near the transverse center line Q-Q than the first graphics display region 23, the second graphics display region 24 is formed, in which the character fans with the paper fan. The wearer visually recognizes a combination of these two graphics as if the slits have been opened up to form the through-holes 27 by fanning operation of the character and the wind blows from these through-holes 27.

According to this second embodiment, the front waist region 5 is formed with both the first graphics display region 23 and the second graphics display region 24 so that the graphics reliably get into the wearer and attract his or her interest.

While the first graphics display region 23 and the second graphics display region 24 are formed only on the front waist region elastic member 28 according to this second embodiment, it is possible to form the first graphics display region 23 and the second graphics display region 24 on the front and rear waist regions elastic member 28, 29 both formed with the slits 16.

The invention claimed is:

1. An absorbent article comprising a chassis having a longitudinal direction, a transverse direction, a skin-facing side, a garment-facing side, a front waist region, a rear waist region and a crotch region extending between said front and rear waist regions, these three regions arranged continuously in said longitudinal direction; and a waist region elastic member attached under tension along an end of at least one of said front and rear waist regions, wherein:
   said waist region elastic member includes slits extending in said longitudinal direction therethrough in its thickness direction and said slits are adapted to be stretched in said transverse direction under the effect of said waist region elastic member to form through-holes; and
   said waist region elastic member further includes a first graphics display region defined on said garment-facing side in combination with respective peripheries of said slits so that said first graphics display region cooperates with said through-holes to form a graphic art.

2. The absorbent article defined by claim 1 further including a second graphics display region defined on the garment-facing side of said front and/or rear waist region and formed with said slits and a graphic art meaningfully related with the graphic art in said first graphics display region is displayed in said second graphics display region.

3. The absorbent article defined by claim 1 wherein said chassis includes an inner sheet defining a skin-facing side and an outer sheet defining a garment-facing side and wherein said waist region elastic member is sandwiched between said inner and outer sheets and said through-holes extend through said inner and outer sheets also in the thickness direction thereof.

4. The absorbent article defined by claim 1 wherein said first and second graphics display regions are formed on said front waist region.

* * * * *